( 12 ) United States Patent
Hoppel et al.

(10) Patent No.: US 8,626,263 B2
(45) Date of Patent: Jan. 7, 2014

(54) METHODS AND APPARATUS FOR RELATIVE PERFUSION AND/OR VIABILITY

(75) Inventors: Bernice Eland Hoppel, Delafield, WI (US); Paul Edgar Licato, Wauwatosa, WI (US); Amy Lynette Broadie, West Allis, WI (US); Tracy Quayle Callister, Hendersonville, TN (US)

(73) Assignee: General Electric Company, Schenectady, NY (US)

( * ) Notice: Subject to any disclaimer, the term of this patent is extended or adjusted under 35 U.S.C. 154(b) by 2347 days.

(21) Appl. No.: 11/403,656

(22) Filed: Apr. 13, 2006

(65) Prior Publication Data

US 2007/0244389 A1    Oct. 18, 2007

(51) Int. Cl.
*A61B 5/05* (2006.01)

(52) U.S. Cl.
USPC ........... 600/407; 600/410; 600/436; 600/437; 600/431; 378/4; 378/5

(58) Field of Classification Search
USPC .......... 600/436, 407, 410, 431, 437; 378/4, 5, 378/98.9, 19
See application file for complete search history.

(56) References Cited

U.S. PATENT DOCUMENTS

| 5,754,676 | A | 5/1998 | Komiya et al. | |
|---|---|---|---|---|
| 5,812,691 | A * | 9/1998 | Udupa et al. | 382/128 |
| 6,671,541 | B2 * | 12/2003 | Bishop et al. | 600/436 |
| 6,836,528 | B2 | 12/2004 | Reddy et al. | 378/5 |
| 6,898,263 | B2 | 5/2005 | Avinash et al. | 378/4 |
| 6,918,769 | B2 | 7/2005 | Rink | |
| 7,031,426 | B2 | 4/2006 | Iatrou et al. | |
| 7,058,210 | B2 | 6/2006 | Mundy et al. | |
| 2004/0063083 | A1 | 4/2004 | Rink | |
| 2005/0043614 | A1 | 2/2005 | Huizenga et al. | |
| 2005/0096528 | A1 | 5/2005 | Fritz et al. | |
| 2006/0052690 | A1 | 3/2006 | Sirohey et al. | 600/420 |

FOREIGN PATENT DOCUMENTS

| JP | 2000-126178 A | 5/2000 |
|---|---|---|
| JP | 2003-010171 A | 1/2003 |
| JP | 2003-225231 A | 8/2003 |
| JP | 2004-105728 A | 4/2004 |
| JP | 2005-095340 A | 4/2005 |
| JP | 2005-245734 A | 9/2005 |

(Continued)

OTHER PUBLICATIONS

Author: Yasushi Koyama, MD et al.; Journal of Magnetic Resonance Imaging; Computed Tomography Assessment of Myocardial Perfusion, Viability, and Function; Date: 2004; pp. 800-815 (16 pages).

(Continued)

*Primary Examiner* — Joel Lamprecht
(74) *Attorney, Agent, or Firm* — ZPS Group, SC

(57) ABSTRACT

A method of evaluating tissue of an organ includes performing at least one of classification processing and clustering processing to obtain a processed dataset to visualize at least one of the imaging agent, blood, the contrast agent, and the biomedical agent distribution in the tissue, a relative regional uptake of the at least one of the imaging agent, blood, the contrast agent, and the biomedical agent in the tissue, relative regional flow of the at least one of the imaging agent, blood, the contrast agent, and the biomedical agent and the clearance or persistence of the at least one of the imaging agent, blood, the contrast agent, and the biomedical agent within the tissue and the characterization of elemental components of disease.

22 Claims, 3 Drawing Sheets

Block Diagram Representative of an Imaging System with an Associated Display

(56) References Cited

FOREIGN PATENT DOCUMENTS

| JP | 2006-042998 A | 2/2006 |
|----|---------------|--------|
| JP | 2006-246941 A | 9/2006 |
| WO | 2006-056954 A2 | 6/2006 |

OTHER PUBLICATIONS

Author: Ronald L. Wolf et al.; Arteriosclerosis, Thrombosis, and Vascular Biology; Mineral Volume and Morphology in Carotid Plaque Specimens Using High-Resolution MRI and CT; Date: Jun. 9, 2005; pp. 1728-1735 (8 pages).

Author: Yasushi Koyama, MD et al.; Radiology; Assessment of Reperfused Acute Myocardial Infarction with Two-Phase Contrast-enhanced Helical CT: Prediction of Left Ventricular Function and Wall Thickness; Date: Aug. 16, 2004; pp. 804-811 (8 pages).

Mendizabal-Ruiz et al., "A probabilistic segmentation method for the identification of luminal borders in intravascular ultrasound images," IEEE, 2008, pp. 1-8.

Naito et al., "Cardiovascular CT: Cardiomyopathies," Clinical All-round, 47(6), 1989-1996 (1998).

Japanese Office Action for JP2007-293848, TPO-5367, Apr. 23, 2013.

\* cited by examiner

Block Diagram Representative of an Imaging System with an Associated Display ation of a contrast agent. This allows for the visualization of the perfusion or blood flow through regions of myocardium that may be affected. Regions lacking microvasculature flow show up as hypo-enhancement due to the lack of contrast agent flowing through that area. The large or moderate perfusion defects can be measured using nuclear imaging, but also can be evaluated with greater resolution using a simple low dose technique. This technique is based on the uptake of the contrast agent in the myocardium. Normal myocardium shows a more rapid uptake of contrast agent with a fairly rapid washout. The slightly damaged and less perfused tissue will gradually reach maximum uptake of contrast agent. However, there will be a time differential between the normal myocardium and the slightly injured myocardium. The more injured myocardium will never have maximum uptake of contrast agent due to lack of perfusion and it will take a greater amount of time to washout.

METHODS AND APPARATUS FOR RELATIVE PERFUSION AND/OR VIABILITY

BACKGROUND OF THE INVENTION

This invention relates generally to methods and apparatus for Diagnostic Imaging (DI), and more particularly to methods and apparatus that provide for 3D and 2D relative perfusion viability.

When a patient comes into an emergency room or other clinical setting and is being evaluated for a possible heart attack there are usually three possible outcomes concerning myocardial health. 1. No disease (and a doctor is not going to treat the patient), 2. Positive disease (minor disease, and the doctor will typically treat with medication(s)), and 3. Positive disease (major disease, and the doctor typically treats with revascularization such as Coronary Artery Bypass Grafting (CABG) or angioplasty (AP)).

A simple Computed Tomography (CT) angiography can determine if there is no disease present. However, additional information is needed to determine the severity of the disease if disease is present.

CT uses both anatomical and functional methods to determine the perfusion and viability of the myocardium. CT also provides functional information about flow through microvasculature within the myocardium imaging following the injection of a contrast agent. This allows for the visualization of the perfusion or blood flow through regions of myocardium that may be affected. Regions lacking microvasculature flow show up as hypo-enhancement due to the lack of contrast agent flowing through that area. The large or moderate perfusion defects can be measured using nuclear imaging, but also can be evaluated with greater resolution using a simple low dose technique. This technique is based on the uptake of the contrast agent in the myocardium. Normal myocardium shows a more rapid uptake of contrast agent with a fairly rapid washout. The slightly damaged and less perfused tissue will gradually reach maximum uptake of contrast agent. However, there will be a time differential between the normal myocardium and the slightly injured myocardium. The more injured myocardium will never have maximum uptake of contrast agent due to lack of perfusion and it will take a greater amount of time to washout.

Additionally, a technique called delayed hyper-enhancement CT can be employed to reveal the extent of injured myocardium in dysfunctional myocardial tissue, hence the capability of recovering contractile function once blood flow delivering oxygen and substrates is restored, either spontaneously or following revascularization. In delayed hyper-enhancement, an additional agent is infused either continuously or as a bolus via an intravenous route and an image is taken 10-15 minutes following infusion. In normal myocardium, the infused contrast agent is excluded from intracellular compartments, however, in injured myocardium, the sarcolemmal membrane of myocytes become permeable allowing contrast agent to accumulate, which results in the observed hyper-enhancement. Thus, lack of contractile function (hypokinesia) and absence of hyper-enhancement (preserved integrity of the sarcolemmal membrane of myocytes) may indicate the presence of hibernating myocardium, which is likely to improve after revascularization of the artery supplying that particular territory. CT imaging using the above, described combination of anatomical and functional methods may reliably differentiate areas of hibernating (viable) from infracted (non-viable) myocardium following a heart attack.

Measuring the signal intensity changes allows one to evaluate for a possible perfusion deficit or hyper-enhancement, thereby indicating abnormal tissue.

When one images the myocardium, the peak uptake of the normal myocardium, which is measured by the timing bolus, there is the greatest differential between normal myocardium and damaged myocardium. For those pixels that have an intensity level in an overlap region as explained in greater detail below, the clustering algorithm herein described helps to discriminate which bin it belongs to. In other words, an isolated pixel or two in the overlap region may not be statistically significant.

BRIEF DESCRIPTION OF THE INVENTION

In one aspect, a method of evaluating tissue of an organ is provided. The method includes accessing image data from an imaging modality acquisition system wherein the image data includes at least one of a three dimensional single phase dataset and a three dimensional multi-phase dataset of a feature of interest in an organ including tissue wherein the data is acquired in conjunction with at least one of an imaging agent, blood, a contrast agent, and a biomedical agent. The method also includes performing at least one of statistical processing and clustering processing to obtain a processed dataset to visualize at least one of the imaging agent, blood, the contrast agent, and the biomedical agent distribution in the tissue, a relative regional uptake of the at least one of the imaging agent, blood, the contrast agent, and the biomedical agent in the tissue, relative regional flow of the at least one of the imaging agent, blood, the contrast agent, and the biomedical agent and the clearance or persistence of the at least one of the imaging agent, blood, the contrast agent, and the biomedical agent within the tissue.

In another aspect, a method of evaluating components of a disease is provided. The method includes accessing image data from any imaging modality system wherein the image data includes either a three dimensional, single or multi-phase dataset of data. The method also includes statistical or clustering processing to visualize and characterize the components of the tissue or organ for evaluation of disease.

In still another aspect, an imaging system includes an acquisition device configured to receive at least one of transmitted energy through a patient and emitted energy from a patient, and a computer coupled to the acquisition device. The computer is configured to do at least one of a) and b), wherein a) includes accessing image data from the acquisition device, wherein the image data includes a three dimensional, single or multi-phase dataset of data, and statistical or clustering processing to visualize and characterize the components of the tissue or organ for evaluation of disease. Wherein b) includes accessing image data from an imaging modality acquisition system wherein the image data includes at least one of a three dimensional single phase dataset and a three dimensional multi-phase dataset of a feature of interest in an organ including tissue wherein the data is acquired in conjunction with at least one of an imaging agent, blood, a contrast agent, and a biomedical agent, and perform at least one of statistical processing and clustering processing to obtain a processed dataset to visualize at least one of the imaging agent, blood, the contrast agent, and the biomedical agent distribution in the tissue, a relative regional uptake of the at least one of the imaging agent, blood, the contrast agent, and the biomedical agent in the tissue, relative regional flow of the at least one of the imaging agent, blood, the contrast agent, and the biomedical agent and the clearance or persistence of the at least one of the imaging agent, blood, the contrast agent, and the biomedical agent within the tissue.

DETAILED DESCRIPTION OF THE INVENTION

There are herein provided clustering and classification methods and apparatus useful for imaging systems such as, for example, but not limited to a Computed Tomography (CT) System. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of CT, it is contemplated that the benefits of the invention accrue to all DI modalities including Magnetic Resonance Imaging (MRI), Positron Emission Tomography (PET), Electron Beam CT (EBCT), Single Photon Emission CT (SPECT), Ultrasound, optical coherence tomography, etc.

Figure 1:
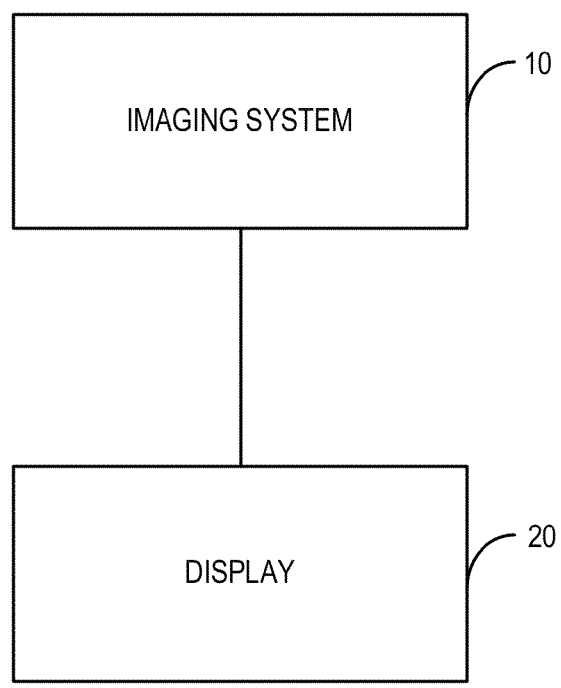
FIG. 1 illustrates an imaging modality acquisition system with an associated display.

FIG. 1 illustrates an imaging modality acquisition system 10 with an associated display 20. Imaging system 10 can be of any modality, but in one embodiment, system 10 is a CT system. In another embodiment, system 10 is a dual modality imaging system such as a combined CT/PET system and the below described clustering and statistical methods can be done in one modality (e.g., CT) and the processed data can be transferred to the other modality (e.g., PET). Display 20 can be separate from system 10 or integrated with system 10. System 10 includes an acquisition device such as an x-ray radiation detector, a Gamma Camera, and/or an ultrasound probe or RF Coil. Note that in CT, EBCT, and ultrasound the acquisition device receives energy transmitted through the patient, but in PET and SPECT, the acquisition device receives energy emitted from the patient. In MRI, energy is transmitted and a passive signal from this is received. Common to all modalities is that an acquisition device receives energy regarding the patient or other scanned object.

Figure 2:
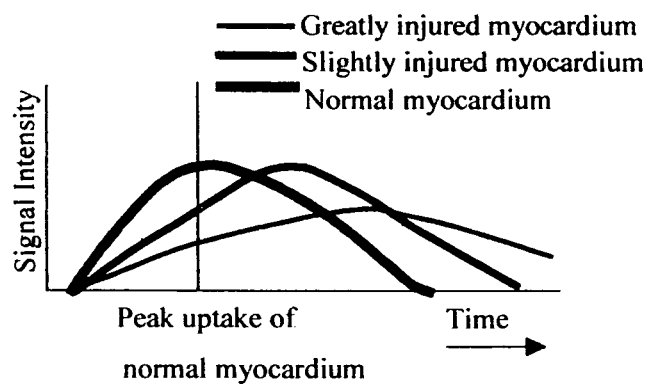
FIG. 2 illustrates the different peak uptake of agent/blood in greatly injured myocardium, slightly injured myocardium, and normal myocardium.
Figure 3:
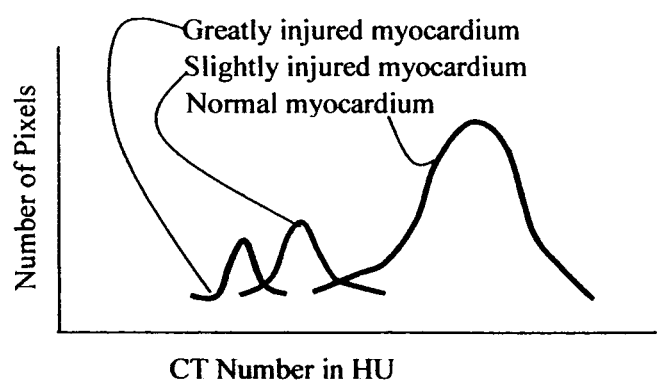
FIG. 3 illustrates the overlap in CT number (in Hounsfield Units HU) from the different tissues as set forth with respect to FIG. 2.
Figure 4B:
FIG. 4 illustrates in part (a) a cluster image of a right coronary artery (RCA) occlusion in accordance with the herein described methods and apparatus, and in part (b) a standard axial image.
Figure 4A:
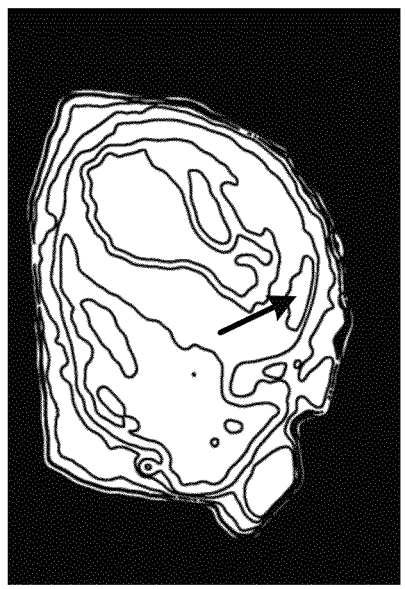

FIG. 2 illustrates the different peak uptake of agent/blood in greatly injured myocardium, slightly injured myocardium, and normal myocardium. FIG. 3 illustrates the overlap in CT number (in Hounsfield Units HU) from the different tissues as set forth with respect to FIG. 2. FIG. 4 illustrates in part (a) a cluster image of a right coronary artery (RCA) occlusion in accordance with the herein described methods and apparatus, and in part (b) a standard axial image.

This herein described methods and apparatus are based on the premise that one must separate out minor differences in signal intensity between regions of the myocardium or other tissues. Damaged myocardium display as either hypo-enhanced or hyper-enhanced compared with normal myocardium. One can see in FIG. 3 that some of the pixels overlap regions. This is where it becomes difficult to differentiate the region of tissue that a particular pixel belongs to. There are multiple methods to use for differentiating pixel intensities. Herein disclosed are protocols and methods of post-processing the images which will help determine the relative regional blood flow.

An image can be displayed on a color scale and a mean pixel intensity and standard deviation can be calculated and either a z-score or a T-test can be used to determine the probability that there is a difference in the values between the myocardium and the tissue in question. One can assign a pixel value by where it falls in a Gaussian or Normal distribution.

$$Z = \frac{\overline{X} - \mu}{\sigma / \sqrt{N}} \text{ or } T = \frac{\overline{X_1} - \overline{X_2}}{\sigma \sqrt{\frac{1}{N_1} + \frac{1}{N_2}}} \quad \text{Equation 1}$$

Additionally, the z-score/T-test can be run with or without the clustering algorithm to determine the probability that the injured myocardium is significantly different than the normal myocardium. The probabilities or the Z-score themselves can be mapped on an image. Mapping probabilities within the range of the myocardium or other types of tissues allows for improved visualization of the area of interest.

Cluster analysis divides data into groups (clusters) such that similar data objects (those of similar signal intensity) belong to the same cluster and dissimilar data objects to different clusters. The resulting data partition improves data understanding and reveals its internal structure. Partitional clustering algorithms divide up a dataset into clusters or classes, where similar data objects are assigned to the same cluster whereas dissimilar data objects should belong to different clusters.

The problem with using a simplistic method like K-means analysis is that choosing the initial centroids of the cluster will determine the outcome.

In medical applications there is very often no sharp boundary between clusters so that fuzzy clustering is often better suited for image data. Membership degrees between zero and one are used in fuzzy clustering instead of crisp assignments of the data to clusters. Fuzzy clustering allows one to calculate a membership function for which each pixel can belong. Each pixel is assigned a value to each cluster somewhere between 0 and 1. The object of the this type of clustering is to minimize the distance between each point and the centroid of the cluster. This is done through an iterative method as described in the equations below.

$$J_m = \sum_{i=1}^{N} \sum_{j=1}^{c} u_{ij}^m \|x_i - c_j\|^2 \quad \text{Equation 2}$$

$$u_{ij} = \frac{1}{\sum_{k=1}^{c} \left(\frac{\|x_i - c_j\|}{\|x_i - c_k\|}\right)^{2/(m-1)}} \text{ where } c_j = \frac{\sum_{i=1}^{N} u_{ij}^m x_i}{\sum_{i=1}^{N} u_{ij}^m} \quad \text{Equation 3}$$

Once a minimum distance is reached the maximum coefficients of each pixel can be displayed as an image.

$$\max\{|u_{ij}^k - u_{ij}^k|\} < \epsilon \quad 0 < \epsilon 1 \text{ where } k=\text{iteration steps} \quad \text{Equation 4}$$

This is just one type of clustering analysis, which can be used to map out the Hounsfield units. Other methods of clustering algorithms can also be employed to this end.

The clustered and scored images can be displayed as either 2D or 3D datasets, which can be reformatted. The 2D sets can be read out in parallel with the other standard gray-scale datasets for comparison. Likewise, the 3D datasets could be placed as colored clusters on top of a transparent 3D dataset. This gives the relative placement of the infarct, which can be correlated with the vascular disease. In addition to, the number of pixels should be able to be counted so that size, transmurality and volume of infarct can be determined. This allows one to calculate the ischemic-burden with the myocardium and develop a scale, which will allow the physician to better determine the severity of the disease.

Furthermore, histogram analysis and/or a mean shift algorithm can be added to the post-processing to increase the speed of it and add additional information. Completing a quick determination of centroid location can improve the speed of the fuzzy clustering algorithm by starting the centroids close to their final location and therefore, reducing the amount of iterations needed to determine the optimal point where they converge to a minimum value.

Additionally, a method of visualization using the 3D dataset would allow for better visualization then using the 2D datasets. The data from the clustering and z-scoring method can be displayed as both a 3D rendered image as well as the reformatted 2D displayed images. This can include the clustered images acting as masks for the standard image data and displayed with a color scale in conjunction with the underlying grayscale image. This allows for more accurate assessment of the transmurality of the defects. The 3D datasets can then be mapped onto a "bulls-eye" to allow those physicians, who are familiar with nuclear medicine, to easily understand the location and extent of disease.

For the clustering, one embodiment uses fuzzy C-Means clustering and the following equation can be used:

$$J = \sum_{i=1}^{c} J_i = \sum_{i=1}^{c} \left( \sum_{k, u_k c_i} \|u_k - c_i\|^2 \right) \quad \text{Equation 5}$$

where c=number of clusters, u=distance of a pixel from cluster centroid.

The membership of a pixel in a cluster is decided as:

$$m_{sk} = \begin{cases} 1 & \text{if } \|u_k - c_i\|^2 \leq \|u_k - c_j\|^2 \\ 0 & \text{otherwise} \end{cases} \quad \text{Equation 6}$$

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

In one embodiment, system 10 includes a device for data storage, for example, a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, a CD-ROM, a DVD or an other digital source such as a network or the Internet, as well as yet to be developed digital means. In another embodiment, the computer executes instructions stored in firmware (not shown). Generally, a processor is programmed to execute the processes described herein. Of course, the methods are not limited to practice in CT and system 10 can be utilized in connection with many other types and variations of imaging systems. In one embodiment, the computer is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Additionally, the computer is operationally coupled to the acquisition device. Although the herein described methods are described in a human patient setting, it is contemplated that the benefits of the invention accrue to non-human imaging systems such as those systems typically employed in small animal research.

Technical effects include obtaining relative perfusion information without the extra dose from a scan. The ability to retrieve flow information with additional dose from extra scans. The ability to provide vascular information at the same time it is providing functional information. And, the visualization and review capabilities in 2 & 3 dimensions for more accurate assessment of the myocardial state.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:

1. A method of evaluating tissue of an organ, said method comprising:
   accessing image data from an imaging modality acquisition system of tissue of an organ;
   performing a three-dimensional segmentation on the image data to isolate a sub-portion of the image data to allow for more accurate processing;
   processing the segmented image data with a statistical classification algorithm;
   identifying an abnormality in the tissue of the organ using the processed data;
   assigning a degree of severity to the abnormality based on the processed data; and
   creating an image visually distinguishing the degree of severity of the abnormality.

2. The method of claim 1 wherein processing the segmented image data comprises performing at least one of a z-scoring of the tissue, a statistical analysis, at least one t-test, a multivariate analysis, a classifier based analysis, an exclusive clustering algorithm, an overlapping and fuzzy clustering algorithm, a partitioning algorithm, a probabilistic clustering, a hierarchical clustering, a K-means analysis, a fuzzy C-means analysis, an expectation maximization analysis, a density based algorithm, a grid-based algorithm, a model based algorithm, and combinations thereof.

3. The method of claim 1 further comprising:
delivering one or two injections to provide classification information of perfusion or viability, wherein the organ is one of a heart, a liver, a brain, a vasculature, and a kidney.

4. The method of claim 1 wherein the abnormality comprises at least one of a volume of ischemic tissue, an area of ischemic tissue infarct, a percentage of ischemic tissue within the organ, an organ wall motion, a relative blood flow to the tissue, a microvasculature density, a microvasculature pattern, at least one calcification, a stroke volume, a mass volume, a percent stenosis, an agent distribution within the organ, an agent clearance throughout the organ, an agent distribution in the tissue, a whole organ uptake of agent, a regional uptake of agent, a regional washout of agent, a regional accumulation of agent, a regional persistence of agent, a regional clearance of agent, a whole organ washout of agent, a clearance in the tissue over a plurality of phases, a thrombosis, a mass shape, and combinations thereof.

5. The method of claim 1 further comprising performing a visualization of the abnormality using a three or four dimensional display of the processed image data represented by at least one of color, texture, and pattern as an overlay of the processed image data.

6. The method of claim 1 further comprising:
comparing the processed image data with one of an originally collected dataset, a curved reformat of the processed dataset, a lumen view of the processed dataset, and combinations thereof; and
performing visualization for preferred presentation to the user including visualization of deficit or hyper intense areas in a three-dimensional display.

7. The method of claim 1 further comprising performing a visualization of the abnormality as a time course in response to physiological motion of the organ or the passage of an imaging agent through the organ over time.

8. The method of claim 1, comprising accessing the image data from one of a single energy CT system and a multi-energy CT system.

9. The method of claim 8 further comprising sending data to one of a PET system, a SPECT system, a MRI system, and an Ultrasound system.

10. The method of claim 1 further comprising performing at least one of reconstructing the image data in an angiographic view for disease evaluation, reformatting the image data for an optimal view or functional characteristics, statistically analyzing a cluster view for disease component analysis, and statistically analyzing the image data for at least one of imaging agent wash-in, clearance, distribution, and accumulation either regionally or globally.

11. The method of claim 1 comprising performing a statistical or a clustering processing to visualize and characterize components of the tissue for evaluation of disease.

12. The method of claim 1 further comprising differentiating between anatomical differences as well as various components of disease.

13. An imaging system comprising:
an acquisition device configured to receive energy regarding an organ; and
a computer coupled to the acquisition device, the computer configured to:
access image data from the acquisition device, wherein the image data comprises a three-dimensional, single or multi-phase set of pixels;
define a plurality of data clusters representing differing ranges of signal intensity;
assign the set of pixels to respective data clusters; and
characterize components of the organ for evaluation of disease based on the pixel assignments.

14. The imaging system of claim 13 wherein the computer is further configured to create an image of the organ wherein the plurality of data clusters are represented by at least one of color, texture, and pattern.

15. The imaging system of claim 14 wherein the computer is further configured to overlay the image as a mask on an underlying grayscale image of the organ.

16. The imaging system of claim 13 wherein the computer is configured to process the image data using at least one of a z-scoring algorithm and a clustering algorithm.

17. A computer readable storage medium having a computer program stored thereon and representing a set of instructions that when executed by a computer cause the computer to:
access an initial image dataset comprising a plurality of pixels corresponding to a tissue;
segment the initial image dataset to isolate a portion of the tissue;
process the segmented image dataset using a classifying algorithm;
identify levels of ischemia corresponding to the plurality of pixels from the processed image dataset; and
create a processed image using the processed image dataset, the processed image having a plurality of visually distinct areas corresponding to the levels of ischemia of the plurality of pixels.

18. The computer readable storage medium of claim 17 wherein the set of instructions cause the computer to process the segmented image dataset using at least one of a z-scoring algorithm and a clustering algorithm.

19. The computer readable storage medium of claim 17 wherein the set of instructions further cause the computer to:
identify a number of pixels of the plurality of pixels corresponding to an infarct; and
determine one of a size, a transmurality, and a volume of the infarct.

20. The computer readable storage medium of claim 17 wherein the set of instructions cause the computer to create a processed image having the plurality of visually distinct areas represented by one of differing colors, textures, and patterns.

21. The computer readable storage medium of claim 20 wherein the set of instructions further cause the computer to:
create an initial image corresponding to the initial data set; and
overlay the processed image as a mask on the initial image.

22. The computer readable storage medium of claim 17 wherein the set of instructions further cause the computer to:
access the initial image dataset of the tissue from an imaging system of a first modality;
access a second image dataset of the tissue from an imaging system of a second modality;
create a secondary image of the tissue from the second image dataset; and
overlay the processed image as a mask on the secondary image.

* * * * *